United States Patent [19]

Kenna

[11] Patent Number: 4,583,270

[45] Date of Patent: Apr. 22, 1986

[54] RASP HANDLE

[75] Inventor: Robert V. Kenna, Hackensack, N.J.

[73] Assignee: Pfizer Hospital Products Group, Inc., New York, N.Y.

[21] Appl. No.: 485,368

[22] Filed: Apr. 15, 1983

[51] Int. Cl.⁴ .............................................. B23D 71/04
[52] U.S. Cl. ......................................... 29/80; 30/169; 128/92 E
[58] Field of Search ...................... 279/1 R; 29/80, 78, 29/79; 16/114 R; 128/92 E; 30/169; 7/167, 168; 81/428 R, 428 PG; 76/36

[56] References Cited

U.S. PATENT DOCUMENTS

| 645,565 | 3/1900 | Manes | 29/80 X |
|---|---|---|---|
| 2,122,263 | 6/1938 | Pinter | 30/169 |
| 2,353,296 | 7/1944 | Disse | 30/169 |
| 2,975,505 | 3/1961 | Linskey et al. | 29/80 |
| 3,656,216 | 4/1972 | Coon et al. | 29/80 |
| 3,802,077 | 4/1974 | Averitt | 30/169 X |
| 3,964,143 | 6/1976 | Coon | 29/80 |
| 4,263,704 | 4/1981 | Myers et al. | 29/80 |
| 4,306,550 | 12/1981 | Forte | 128/92 E |

Primary Examiner—Gil Weidenfeld
Assistant Examiner—Glenn L. Webb
Attorney, Agent, or Firm—Charles J. Knuth; Peter C. Richardson; Harold W. Ordway

[57] ABSTRACT

A rasp handle has an elongate body portion with a pistol-type grip extending therefrom and rasp retaining structure at its front end. Such structure includes a fixed jaw and a slide jaw constructed and arranged for sliding movement relative to the fixed jaw between a forward closed locking position where a rasp is locked between the jaws and a rearward open rasp receiving and releasing position. A lever is connected to shift the slide jaw between its closed and open positions. A pivot interconnects the lever and the slide jaw so that the lever is free to move between a locked position adjacent the body portion and an unlocked jaw manipulating position away from the body portion.

10 Claims, 10 Drawing Figures

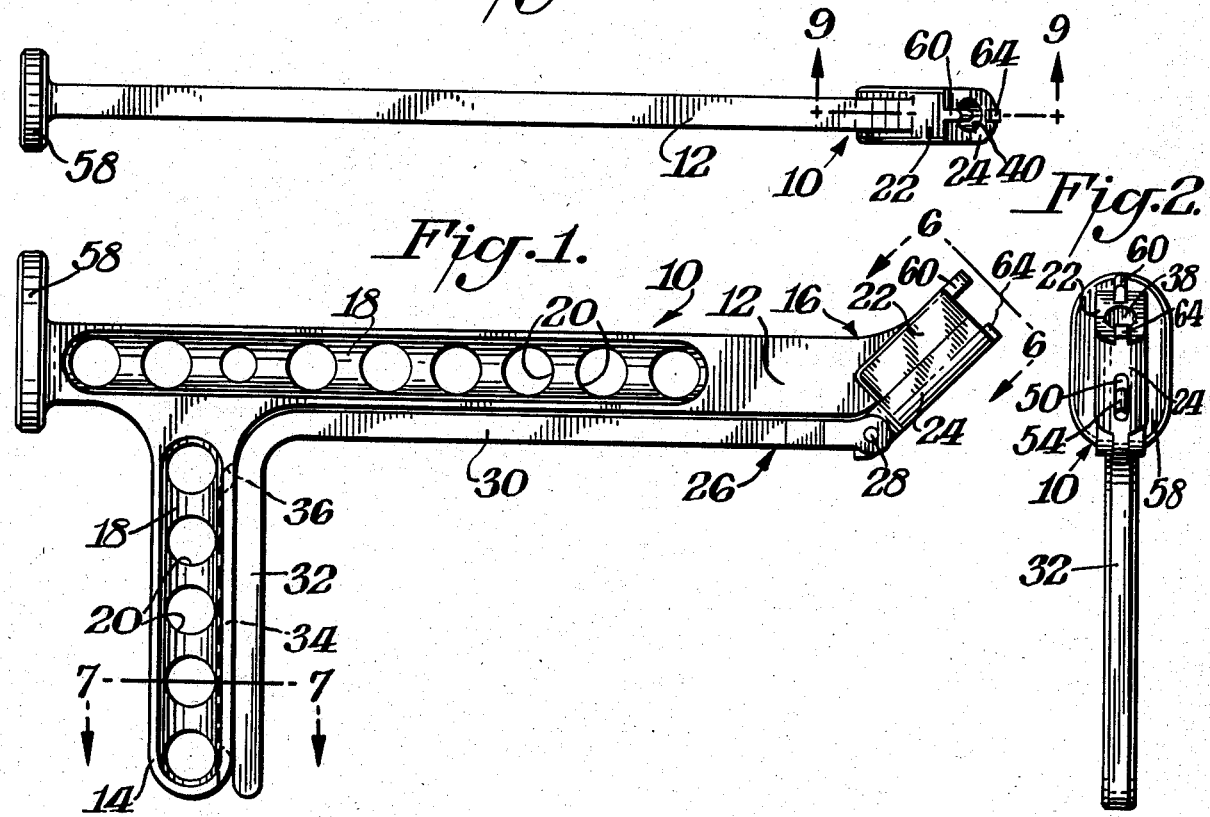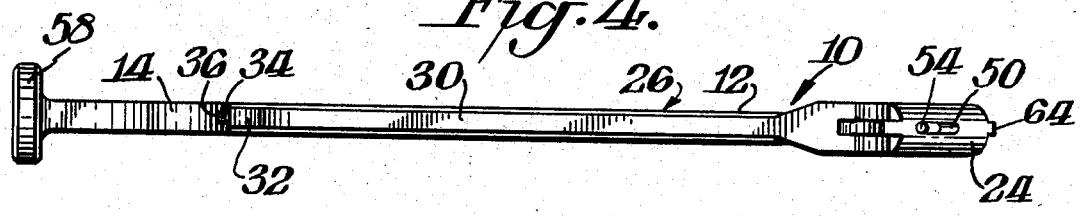

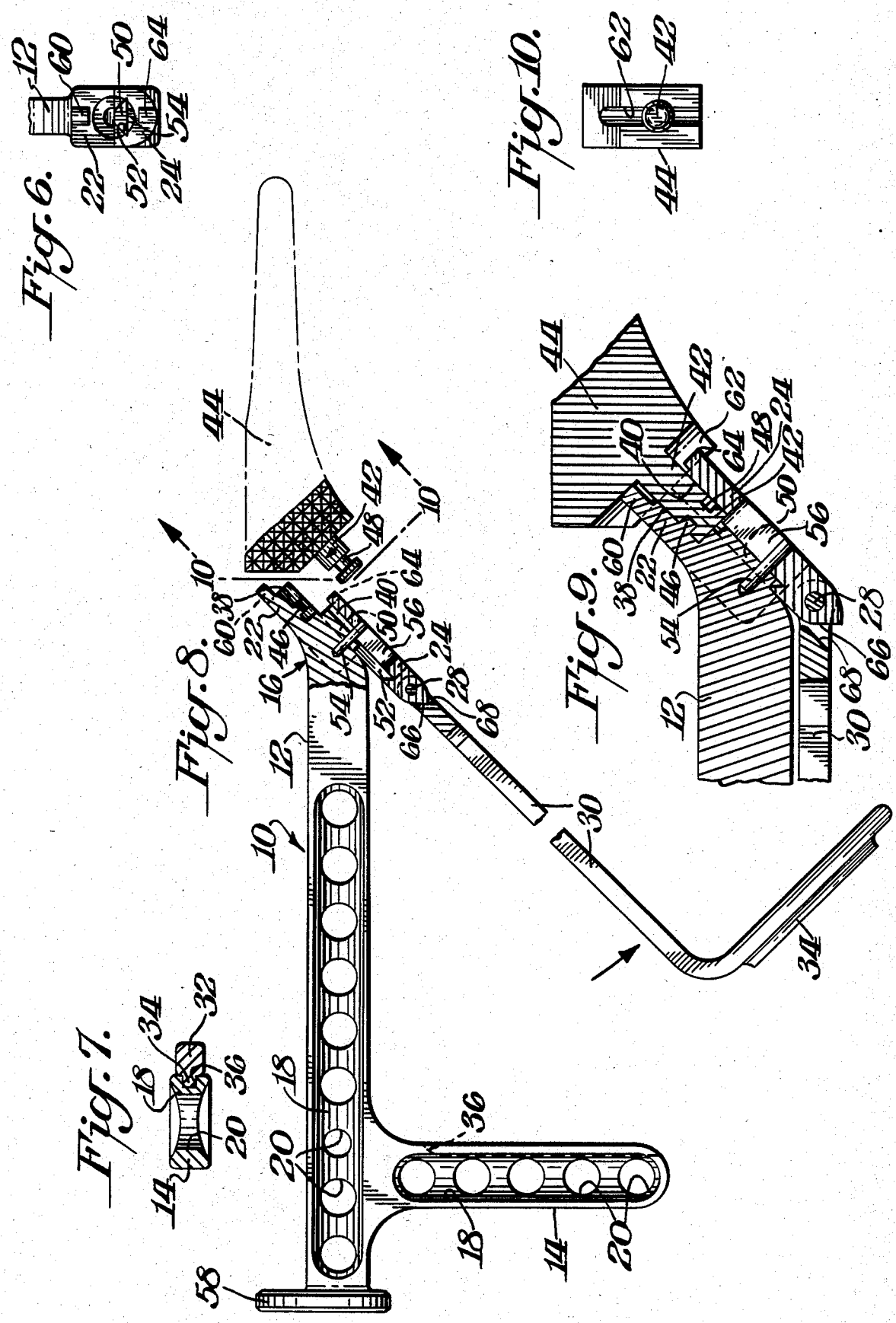

RASP HANDLE

BACKGROUND OF THE INVENTION

The present invention relates to a rasp handle, and more particularly to a handle for releasably retaining and manipulating a rasp during use thereof.

Hip arthroplasty procedure includes anesthesia and patient placement on a table in proper orientation. The patient's body is then stabilized, scrubbed, prepped and draped. An incision is made and the subcutaneous tissue is divided. Appropriate soft tissue is excised and/or divided for exposure and dislocation of the hip. After the femoral head is dislocated from its associated acetabulum, the head is rotated for better exposure. A femoral neck osteotomy is then performed wherein the neck and head are cut away from the femur shaft. Next, the cancellous bone is removed from the intermedullary canal by means of a rasp or reamer device. In some cases, a separate handle is used with the rasp.

SUMMARY OF THE INVENTION

Accordingly, it is an object of the present invention to provide a rasp handle which is highly effective in retaining and manipulating a rasp tool during use thereof and which is easily released from the rasp following such use.

In accordance with the present invention, a rasp handle has an elongate body portion with a pistol-type grip extending therefrom and rasp retaining structure at the front end thereof. The rasp retaining structure includes a fixed jaw and a slide jaw arranged for sliding movement relative to the fixed jaw between a forward closed locking position where a rasp is locked between the jaws and a rearward open rasp receiving and releasing position. A lever is connected to shift the slide jaw between its closed and open positions. A pivot interconnects the lever and the slide jaw whereby the lever is free to move between a locked position adjacent the body portion and an unlocked jaw manipulating position away from the body portion.

Preferably, the lever has a rear end portion positioned adjacent the pistol-type grip when the slide jaw is in its forward closed position and the lever is in its locked position adjacent the body portion. This structural arrangement prevents the jaws from sliding open except when the lever is pivoted to its unlocked jaw manipulating position away from the body portion. The rear end portion of the lever may include a rearwardly facing tongue and the pistol-type grip may include a groove arranged to receive the tongue when the lever is in its locked position.

The fixed jaw includes an internal undercut arranged for mating engagement with a rasp, and the slide jaw includes an internal abutment surface adapted to hold the rasp in mating engagement with the undercut when the slide jaw is in its forward closed position and the rasp is locked between the jaws. In the preferred embodiment, the fixed and slide jaws each include a semicylindrical recess that together form a cylindrical rasp receiving recess when the slide jaw is in its forward closed position. An internal semiannular rib on the fixed jaw extends into the semicylindrical recess to provide the internal undercut. Moreover, the cylindrical rasp receiving recess has a longitudinal axis disposed approximately 45° to the body portion of the handle.

Preferably, a dovetail sliding connection is provided between the fixed and slide jaws, and a stop limits the movement of the slide jaw between its forward closed and rearward open positions relative to the fixed jaw.

In the preferred embodiment, the lever has a front end portion parallel to and adjacent the body portion, and a rear end portion disposed substantially perpendicular to the front end portion and parallel to and adjacent the pistol-type grip, when the lever is in its locked position. Moreover, the body portion of the rasp handle may include a strike plate at the rear end thereof to assist in using a rasp when retained by the handle.

BRIEF DESCRIPTION OF THE DRAWINGS

Novel features and advantages of the present invention in addition to those mentioned above will become apparent to those skilled in the art from a reading of the following detailed description in conjunction with the accompanying drawing wherein similar reference characters refer to similar parts and in which:

FIG. 1 is a side elevational view of a rasp handle according to the present invention;

FIG. 2 is a front end elevational view of the rasp handle shown in FIG. 1;

FIG. 3 is a top plan view of the rasp handle shown in FIG. 1;

FIG. 4 is a bottom plan view of the rasp handle shown in FIG. 1;

FIG. 5 is a rear end elevational view of the rasp handle shown in FIG. 1;

FIG. 6 is an elevational view of the rasp retaining structure at the front end of the rasp handle viewed in the direction of line 6—6 of FIG. 1;

FIG. 7 is a sectional view taken along line 7—7 of FIG. 1;

FIG. 8 is a side elevational view similar to FIG. 1 illustrating the combination of a rasp handle and a rasp, the handle being in its open rasp receiving and releasing position and portions thereof being broken away in order to show interior detail;

FIG. 9 is a sectional view taken along line 9—9 of FIG. 3; and

FIG. 10 is an end elevational view of the rasp shown in FIG. 8 viewed in the direction of line 10—10 of FIG. 8.

DETAILED DESCRIPTION OF THE INVENTION

Referring in more particularity to the drawing, a rasp handle 10 has an elongate body portion 12 with a pistol-type grip 14 extending therefrom. Rasp retaining structure 16 is provided at the front end of the body portion 12 for locking a rasp to the rasp handle 10, as explained more fully below. The rasp handle 10 may be fabricated from stainless steel or similar material by techniques well known in the art. As shown best in FIG. 1, body portion 12 and pistol-type grip 14 each include recesses 18 on opposite sides thereof, and a series of spaced-apart openings 20 are located in the recesses 18. These recesses 18 and openings 20 eliminate unnecessary material from the rasp handle 10 without adversely affecting its overall strength.

The rasp retaining structure 16 at the front end of body portion 12 includes a fixed jaw 22 and a slide jaw 24 arranged for a sliding movement relative to the fixed jaw 22 between a forward closed locking position (FIG. 1) and a rearward open rasp receiving and releasing position (FIG. 8). Such positioning of the jaws 22,24 between closed and open positions functions to retain and release a rasp, as explained more fully below.

A lever 26 is connected to manipulate the slide jaw 24 between its closed and open positions. A pivot 28 interconnects lever 26 and slide jaw 24 so that the lever 26 is free to swing between a locked position adjacent the body portion 12 (FIG. 1) and an unlocked jaw manipulating position away from body portion 12 (FIG. 8).

The lever 26 has a front end portion 30 parallel and adjacent to body portion 12 when the lever 26 is in its locked position shown in FIG. 1. When so positioned, a rear end portion 32 of lever 26 is parallel to and adjacent the pistol-type grip 14. Preferably, the pistol-type grip 14 is disposed substantially perpendicular to body portion 12 of the rasp handle 10, and the rear end portion 32 of lever 26 is substantially perpendicular to the front end portion 30 of the lever 26.

As shown best in FIGS. 1, 7 and 8, rear end portion 32 of lever 26 includes a rearwardly facing tongue 34 and the piston-type grip 14 includes a groove 36 constructed and arranged to receive the tongue 34 when the lever 26 is in its locked position shown in FIG. 1.

Referring to FIGS. 8 and 9, the fixed jaw 22 of the rasp retaining structure 16 includes a semicylindrical recess 38 and the slide jaw 24 includes a similar recess 40. When the slide jaw 24 is in its forward closed locking position, shown in FIG. 9, the semicylindrical recesses 38,40 together form a cylindrical rasp receiving recess for accommodating the shank 42 of a rasp tool 44. To facilitate anchoring the shank 42 within the cylindrical recess, the fixed jaw 22 has an internal semiannular rib 46 that extends into the semicylindrical recess 38. The rib 46 provides an undercut and cooperates with an annular depression 48 on shank 42 to thereby lock rasp 44 to rasp retaining structure 16 when the elements of rasp handle 10 are oriented as shown in FIG. 9. Rib 46 enters the annular depression 48, and the semicylindrical recess 40 on slide jaw 24 provides an internal abutment surface which holds shank 42 in mating engagement with rib 46 to thereby prevent removal of the rasp 44.

The sliding motion between the fixed and slide jaws 22,24 is effected by a dovetail 50 on the fixed jaw 22 which cooperates with a dovetail groove 52 on the slide jaw 24, and a stop limits the movement of the slide jaw 24 between its forward and rearward positions. As shown best in FIGS. 8 and 9, the stop structure comprises a pin 54 connected to and extending from the fixed jaw 22 and a slot 56 in the slide jaw 24 arranged substantially parallel to the dovetail groove 52. The projecting end of pin 54 extends into slot 56, and the movement of slide jaw 24 is limited by engagement of the pin 54 at the forward and rearward ends of the slot 56.

Rasp handle 10 is arranged so that the long axis of the rasp 44 is aligned with or closely parallel to the long axis of body portion 12. Since shank 42 extends at an angle of approximately 45° to the long axis of the rasp 44, the cylindrical rasp receiving recess formed by the semicylindrical recesses 38,40 on the fixed and slide jaws 22,24 has a longitudinal axis which is disposed approximately 45° to body portion 12. Such geometry positions the long axis of rasp 44 in alignment or closely parallel to the long axis of body portion 12. Use of rasp 44 is primarily along the line of its long axis, and a strike plate 58 is provided at the rear end of body portion 12 to assist in driving the rasp 44 in that direction.

Preferably, rasp handle 10 and rasp 44 include interlocking structure which prevents the rasp 44 from moving relative to the rasp handle 10 once the rasp 44 is locked in place. In the embodiment of the invention illustrated in the drawing, such interlocking structure is in the form of a projection 60 on the fixed jaw 22 outwardly extending in a forward direction and arranged to fit within a slotted recess 62 in the rasp 44. Another projection 64 is similarly positioned on the slide jaw 24 for interlocking engagement with recess 62 when the slide jaw 24 is in its forward closed position and the rasp 44 is locked between the jaws 22,24. Also, slide jaw 24 and lever 26 include abutment surfaces 66 and 68, respectively, for limiting outward movement of the lever 26 to its unlocked jaw manipulating position. As shown best in FIGS. 8 and 9, these abutment surfaces 66,68 are adjacent pivot 28.

The rasp handle 10 of the present invention operates in a highly effective manner to retain and manipulate a rasp tool 44 during use thereof, and the rasp handle 10 is easily released from the rasp 44 following such use. FIG. 8 illustrates the rasp handle 10 in its rasp receiving position, it being understood that the rasp handle 10 is similarly positioned during release of the rasp 44. The lever 26 is pivoted to its unlocked jaw manipulating position away from the body portion 12 and pulled in a generally rearward direction to locate the slide jaw 24 at its rearward open rasp receiving position. Next, shank 42 is moved in the direction of the arrow until rib 46 is disposed in the annular depression 48 on shank 42. The slide jaw 24 is then shifted to its forward closed rasp locking position by moving lever 26 in a generally forward direction until stop pin 54 engages the rear end of slot 56. The surface of semicylindrical recess 40 on slide jaw 24 abuts shank 42 to thereby lock rasp 44 to rasp handle 10, and the interlocking structure 60,62,64 prevents relative movement between the rasp handle 10 and the rasp 44. Finally, lever 26 is pivoted to its locked position adjacent body portion 12 and tongue 34 on the rear end portion 32 of lever 26 enters groove 36 in the pistol-type grip 14. As shown best in FIG. 1, the rear end portion 32 of lever 26 is positioned adjacent the pistol-type grip 14, which locks lever 26 in place and thereby prevents slide jaw 24 from sliding open until lever 26 is pivoted to its jaw manipulating position away from body portion 12. In the latter position, the slide jaw 24 is free to move to its open rasp receiving and releasing position shown in FIG. 8 to thereby facilitate separation of rasp handle 10 from the rasp 44.

I claim:

1. A rasp handle having an elongate body portion with a pistol-type grip extending therefrom and rasp retaining means at the front end thereof, the rasp retaining means including a fixed jaw, a slide jaw constructed and arranged for sliding movement relative to the fixed jaw between a forward closed locking position where a rasp is locked between the jaws and a rearward open rasp receiving and releasing position, a lever connected to shift the slide jaw between its closed and open positions, and pivot means interconnecting the lever and the slide jaw whereby the lever is free to move between a position adjacent the body portion and a position away from the body portion.

2. A rasp handle as in claim 1 wherein the lever has a rear end portion positioned adjacent the pistol-type grip when the slide jaw is in its forward closed position and the lever is positioned adjacent the body portion thereby prevent the jaws from sliding open except when the lever is pivoted to its position away from the body portion.

3. A rasp handle as in claim 2 wherein the rear end portion of the lever includes a rearwardly facing tongue and the pistol-type grip includes a groove constructed and arranged to receive the tongue when the lever is positioned adjacent the body portion.

4. A rasp handle as in claim 1 wherein the fixed jaw includes internal undercut means constructed and arranged for mating engagement with the rasp and the slide jaw includes an internal abutment surface adapted to hold the rasp in mating engagement with the undercut means when the slide jaw is in its forward closed position and the rasp is locked between the jaws.

5. A rasp handle as in claim 4 wherein the fixed and slide jaws each includes a semicylindrical recess that together form a cylindrical rasp receiving recess when the slide jaw is in its closed position, and an internal semiannular rib on the fixed jaw extending into the semicylindrical recess to provide the undercut means.

6. A rasp handle as in claim 5 wherein the cylindrical rasp receiving recess has a longitudinal axis disposed approximately 45° to the body portion.

7. A rasp handle as in claim 1 including a dovetail sliding connection between the fixed and slide jaws, and stop means limiting the movement of the slide jaw between its forward closed and rearward open positions.

8. A rasp handle as in claim 1 wherein the pistol-type grip is disposed substantially perpendicular to the body portion.

9. A rasp handle as in claim 8 wherein the lever has a front end portion parallel to and adjacent the body portion and a rear end portion disposed substantially perpendicular to the front end portion parallel to and adjacent the pistol-type grip when the lever is in its locked position.

10. A rasp handle as in claim 1 wherein the body portion includes a strike plate at the rear end thereof.

* * * * *